United States Patent [19]
Leibinger

[11] Patent Number: 5,797,914
[45] Date of Patent: Aug. 25, 1998

[54] BONE SCREW

[75] Inventor: Karl A. Leibinger, Mulheim, Germany

[73] Assignee: KLS Martin, L.P., Jacksonville, Fla.

[21] Appl. No.: 710,174

[22] Filed: Sep. 12, 1996

[30] Foreign Application Priority Data

Dec. 21, 1995 [DE] Germany ............ 295 20 312 U

[51] Int. Cl.$^6$ .................................................. A61B 17/86
[52] U.S. Cl. ............................ 606/73; 606/79; 411/387
[58] Field of Search ......................... 606/65, 72, 73, 606/79; 411/386, 387

[56] References Cited

U.S. PATENT DOCUMENTS

| | | | |
|---|---|---|---|
| 2,871,752 | 2/1959 | Stern | 411/387 |
| 4,537,185 | 8/1985 | Stednitz | 606/73 |
| 5,098,435 | 3/1992 | Stednitz et al. | 606/73 |
| 5,169,400 | 12/1992 | Muhling et al. | 606/73 |
| 5,199,839 | 4/1993 | DeHaitre | 411/387 |
| 5,334,204 | 8/1994 | Clewett et al. | 606/73 |

*Primary Examiner*—Michael Buiz
*Assistant Examiner*—David O. Reip
*Attorney, Agent, or Firm*—Arthur A. Gardner & Associates, P.C.

[57] ABSTRACT

A bone screw for use in oral, maxofacial, and cranial surgery. The bone screw includes a screw head and body portion. The body portion includes a body tip, the body portion having a single flute being recessed in the area of the body tip and by the area enveloping the thread at the body tip being convex in shape. By this combination of features a bone screw is produced which is very easy to screw in, self-boring and self-tapping.

9 Claims, 1 Drawing Sheet

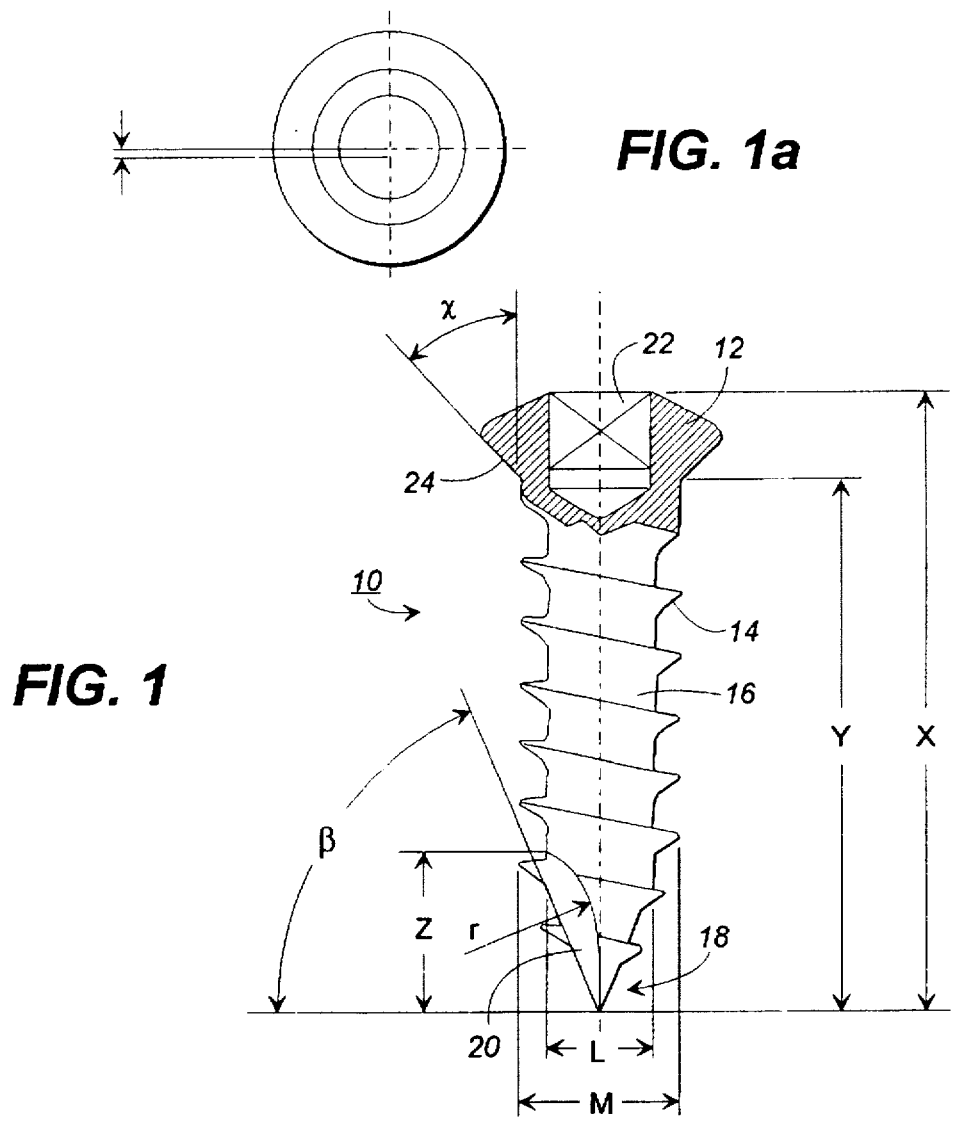
FIG. 1a
FIG. 1
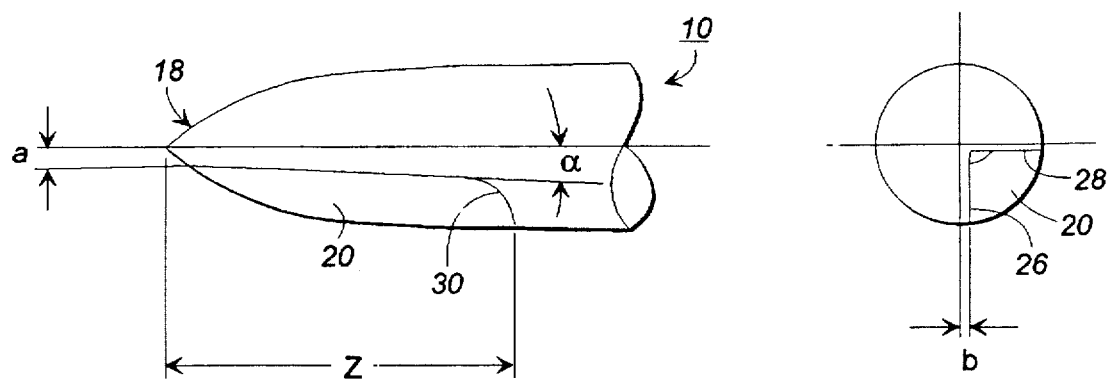
FIG. 2
FIG. 2a

BONE SCREW

TECHNICAL FIELD

The present invention relates to medical apparatus and in particular relates to a bone screw for attaching an item, such as a bone plate, to a bone.

BACKGROUND OF THE INVENTION

In certain surgical procedures, it is necessary to attach an item to a bone. For example, in repairing fractures of the facial bones or of the cranial bones, it is common to use a thin metal bone plate to hold the various pieces together. To use such a bone plate, holes are drilled in the various bone pieces and the bone plate is then secured to the individual bones with bone screws. Disadvantageously, this requires two steps in order to insert the screw: firstly, the hole must be bored in the bone; and secondly, a self-tapping bone screw is screwed into the hole. In addition to requiring additional time during an operation, this also results in a greater number of instruments and other items that have to be sterilized for use. Such bone screws, which are self-tapping, are already known in the prior art. Typical self-tapping bone screws are provided with flutes or cutting grooves in the threaded area, which flutes or cutting grooves, for example, in accordance with the prior art publication No. EP 0 230 856 B 1, run screw-like around the screw axis.

Despite the existence in the art of self-tapping screws, there remains yet a need for a bone screw which can be inserted with a very low moment of rotation (torque), which is self-boring (does not require a pilot hole to be drilled first), and which is self-tapping. It is to the provision of such a bone screw that the present invention is primarily directed.

SUMMARY OF THE INVENTION

Briefly described, in a first preferred form the present invention comprises a bone screw for use in oral, maxofacial, and cranial surgery. The bone screw includes a screw head and body portion. The body portion includes a body tip, the body portion having a single flute being recessed in the area of the body tip and by the area enveloping the thread at the body tip being convex in shape. By means of this combination of features a bone screw is produced which is very easy to screw in, self-boring and self-tapping.

Preferably, the flute is formed by a recess delimited by two walls positioned essentially at right angles to one another. The flute can cover at least a length of the body tip with a convex design.

In accordance with a preferred embodiment, the approximately right-angled recess of the flute at the body tip can first run in the area of the center line and then run out up to the thread along a radius r. Preferably, the radius r is 1–2 mm, most preferably 1.5 mm.

Another preferred embodiment of the invention includes the approximately right-angled recess of the flute at the body tip first running at a transposed distance a to the center line at an angle $\alpha$ to the center line before it runs out up to the thread in a radius. The distance can be approximately 0.05 to 0.4 mm and the angle $\alpha$ can be approximately 3° to 8°, most preferably 5°. In this way, a very good insertion behavior of the screw is achieved.

The length the flute can be 1–3 mm advantageously, most preferably 2 mm.

A bone screw which can be used particularly well for osteosynthesis is produced if the screw head is designed as a countersunk head and if the screw head possesses an internal polygon in a central position. Here an internal polygon designed as a square or as a hexagon has proven to be advantageous as the operating doctor can thereby easily fix the bone screw to his insertion tool while screwing it into the bone.

Further details and advantages of the invention result from the multiple embodiments shown in the accompanying drawings.

BRIEF DESCRIPTION OF THE DRAWING FIGURES

FIG. 1 is an illustration of a partial section of a bone screw in accordance with a first embodiment of the present invention.

FIG. 1a is a bottom view of the bone screw in accordance with FIG. 1 (shown from below).

FIG. 2 is a schematic side view of the tip of a bone screw according to a second preferred embodiment of the present invention.

FIG. 2a is a schematic cross-section through the tip of the bone screw in accordance with FIG. 2.

DETAILED DESCRIPTION OF THE PREFERRED EMBODIMENTS

Referring now in detail to the drawing figures, wherein like reference numerals represent like parts throughout the several views, FIG. 1 shows a bone screw 10 according to a preferred form of the invention. The bone screw 10 in the embodiment in accordance with FIG. 1 consists of a screw head 12 and a body 16 provided with a thread 14 and with a body tip 18. In the area of the body tip a flute 20 has been recessed.

The total length X of the bone screw 10 preferably is between 4 and 19 mm. The length Y of the body preferably is between 2.97 and 17.97 mm. With this screw length, the length of the flute Z preferably is 2 mm. In accordance with the illustrative representation according to FIG. 1, the screw tip 18 is designed in the form of a cone at an angle $\beta$ of 67.5°. The jacket of the thread in the area of the body tip is convex in design as is also shown in schematic form by means of the embodiment in accordance with FIG. 2. In the area above the body tip 18, the diameter of the body with thread M preferably is approximately 2 mm and the diameter of the body without thread L preferably is approximately 1.3 mm. In the embodiment in accordance with FIG. 1, the flute 20 is formed by a recess delimited by two walls formed essentially at right angles to one another. This approximately right-angled recess of the flute runs on the body tip 19, first in the area of the center line and then along a radius r, which preferably is approximately 1.5 mm here, up to the thread.

The screw head 12 is designed as a countersunk screw with the lower flank of the screw head 24 being canted at an angle $\alpha$ of approximately 45° to the center line of the bone screw. An inner square 22 is formed centrally to the center line of the bone screw, which inner square 22 is used to accept a correspondingly shaped screwing tool.

The bone screw comprises a bone-compatible material, for example $TiAl_6V_4$.

In the modified embodiment shown in FIG. 2 and FIG. 2a, the self-boring and self-tapping bone screw 10 essentially corresponds to that in accordance with the embodiment according to FIG. 1. It differs however in the position and design of the flute 20. Basically, the flute 20 preferably is here also formed by a recess formed by two walls 26 and 28 positioned essentially at right-angles to one another (cf FIG. 2a). The approximately right-angled recess of the flute is, however, at the body tip 18 first at a distance a to the center line and runs at an angle α to the center line. Here, the distance a preferably is approximately 0.05 to 0.4 mm, while the angle α preferably is approximately 3° to 8° and most preferably approximately 5° in this embodiment. The length Z can vary between 1 and 3 mm. Towards the thread the flute again runs out through a radius 30. In the sectional representation in accordance with FIG. 2a it can be seen that the flute 20 has the form of a quarter circle, where this can be transposed by a distance b from the perpendicular planes delimiting the quarter circles. The distance b can vary between 0 and 0.2 mm.

Bone screws made in accordance with these constructions have proven to be extremely useful. This is so because such bone screws can be used in surgery procedures without the necessity of first drilling a pilot hole for receiving the bone screw. This greatly reduces the time involved in such surgical procedures. This also simplifies such procedures and reduces the amount of medical equipment that has to be sterilized for such operations. Such bone screws have also proven to be easily inserted into the bone using low moments of rotation (low torques).

Such bone screws have good application in delicate surgery, such as in repairing fractures or other surgical procedures in the fields of oral surgery, maxofacial surgery, and cranial skeletal surgery.

While the invention has been disclosed in preferred forms, it will be apparent to those skilled in the art that many modifications, additions, and deletions can be made therein without departing from the spirit and scope of the invention as set forth in the following claims.

I claim:

1. A self-drilling and self-tapping bone screw for insertion into a bone, said bone screw comprising:

a screw head; and a solid screw body extending from said screw head and including a tapered tip portion terminating at a pointed tip distal from said screw head and a shaft extending from said screw head to said tip portion, said screw body having a centerline and being provided with a continuous thread formed on said shaft and on said tip portion, said tip portion being provided with a recessed flute defined by two walls positioned essentially at a right-angle to one another, wherein a substantial portion of at least one of said two walls comprises a generally flat portion which extends from adjacent said pointed tip toward said screw head at a transposed distance from said centerline and at an acute angle to said centerline, and wherein adjacent said tip portion a profile of said continuous thread is convex.

2. A bone screw in accordance with claim 1, wherein said recessed flute extends longitudinally at least a length of said tip portion.

3. A bone screw in accordance with claim 1, wherein said transposed distance is approximately 0.05 to 0.4 mm and said acute angle is approximately 3° to 8°.

4. A bone screw in accordance with claim 3, wherein said acute angle is approximately 5°.

5. A bone screw in accordance with claim 1, wherein said flute has a length which is approximately 1 to 3 mm.

6. A bone screw in accordance with claim 5, wherein said flute has a length which is approximately 2 mm.

7. A bone screw in accordance with claim 1, wherein said screw head is designed as a countersunk head.

8. A bone screw in accordance with claim 7, wherein said screw head possesses an internal polygon in a centered position.

9. A bone screw in accordance with claim 8, wherein said internal polygon has fewer than six sides.

* * * * *